United States Patent [19]

Drewlow

[11] Patent Number: Plant 6,114

[45] Date of Patent: Feb. 23, 1988

[54] POINSETTIA PLANT NAMED MINNEKEN

[75] Inventor: Lyndon W. Drewlow, Ashtabula, Ohio

[73] Assignee: Mikkelsens Inc., Ashtabula, Ohio

[21] Appl. No.: 824,595

[22] Filed: Jan. 31, 1986

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Schwartz, Jeffery, Schwaab, Mack, Blumenthal & Evans

[57] ABSTRACT

A poinsettia plant named Minneken particularly characterized by the combined characteristics of pink colored bracts, vigorous dwarf growth habit, early flowering, outstanding keeping quality, and by its commercially significant ability of being grown as a single stem or pinched plant.

1 Drawing Figure

The present invention relates to a new and distinctive cultivar of poinsettia plant known by the cultivar name Minneken, and botanically known as *Euphorbia pulcherrima*.

Minneken was developed by me through controlled breeding by crossing Mikkelsen Seedling No. 77-87-11 (seed parent)×Mikkelsen Seedling No. 77-54-2 (pollen parent). Minneken was given the breeding number 78-515-8.

Minneken has been asexually reproduced by me by cuttings in the greenhouses of Mikkelsens Inc., Ashtabula, Ohio, and has been found to retain its distinctive characteristics through successive propagations.

The following characteristics distinguish the new cultivar from its parents and from other poinsettias commercially known and used in the floriculture industry:

1. The bract color of Minneken is a deeper pink than Mikkelpink, disclosed in U.S. Plant Pat. No. 2,501, and the unpatented cultivar Pink Rochford, but is slightly lighter pink in color than Fantastic, disclosed in U.S. Plant Pat. No. 3,721.

2. Minneken is a true genetic dwarf, with short internodes even under high humidity and temperature growing conditions and is thus much more compact than all known existing pink cultivars.

3. The leaf color is lighter green than Fantastic, Mikkelpink and Pink Rochford, and the leaf shape is shorter and broader than the above mentioned cultivars. The leaf margin is smoother and lacks indentations.

4. The flower clusters (cyathia) remain tight and do not grow apart (split) as does Fantastic, Pink Rochford and Mikkelpink.

5. Rooting of cuttings occurs uniformly in 14 to 16 days, which is similar to the other cultivars mentioned.

6. Minneken is similar to Fantastic, Mikkelpink and Pink Rochford in breaking with new lateral shoots when the terminal meristem has been removed; however, Minneken has stronger and thicker stems than the comparison cultivars and is not grassy.

7. The cyathia are retained longer than Fantastic, Pink Rochford and Mikkelpink, and will tolerate lower light, temperature and nutritional stress than the other pink cultivars.

8. The bract number is slightly greater in the involucre than Fantastic, Mikkelpink and Pink Rochford, but the involucre is smaller in diameter due to the genetic dwarf characteristics of this cultivar.

9. The apparent ease of flower initiation and development of cyathia and bracts even under stress environments is of economic importance to both the northern and southern grower.

10. Under natural short days in Ohio, Minneken developed bracts and shed pollen three weeks earlier than Fantastic, Pink Rochford and Mikkelpink. Under controlled day length using black-out cloth, all cultivars flowered nearly the same, indicating that Minneken initiates flowers on a longer critical natural day length.

The accompanying colored photographic drawing, taken as a top view, illustrates the overall appearance of the new cultivar, with the colors being as true as possible to obtain in color reproductions of this type.

The following is a detailed description of the new cultivar based on plants produced under commercial practices in the greenhouses of Mikkelsens Inc., Ashtabula, Ohio, and photographed in December flowering. Color references are made to The Royal Horticultural Society Colour Chart except where general terms of ordinary dictionary significance are used.

Parentage: Controlled breeding by crossing Mikkelsen Seedling No. 77-87-1 (seed parent)×Mikkelsen Seedling No. 77-54-2 (pollen parent).

Propagation:

(A) *Type cutting.*—Stems, 60 to 70 mm.

(B) *Time to root.*—14 to 16 days, 12 to 14 hour day length at 21° C. summer; 16 to 18 days, 12 to 14 hour day length at 21° C. winter.

(C) *Rooting habit.*—Coarse, fibrous, numerous.

Plant description:

(A) *Form.*—Upright; when apical meristem is removed (pinching), leaving 5-6 leaves above the soil line of pot, generally 3 to 5 lateral shoots will emerge.

(B) *Growth habit.*—Compact, true genetic dwarf; short internodes; strong stems that hold the bracts in good placement; growth is vigorous and early propagations may need to be controlled by growth regulators.

(C) *Foliage.*—Leaves are alternate and borne on 3.5 to 4.0 cm. long petioles that have a pinkish tint. (1) Size: Mature leaves are 9 to 10 cm. long and 8 to 9 cm. wide at the broadest point. (2) Shape: Ovate, with leaf apices being acuminate and the base more truncate than rounded. (3) Texture: Glabrous, with veins sunken. (4) Margin: Almost entire, with slight undulate on some leaves. (5) Color: Young foliage top side 146B; under side 146C. Mature foliage top side 137A and; under side 137C.

Flowering description:

(A) *Flowering habits.*—Minneken flowers earlier than most commercial cultivars, apparently having a longer critical day length for flower initiation. Under controlled day length, development time is approximately 10 weeks. Because Minneken is a true genetic dwarf, it is suited for growing as a pinched 10 cm. pot crop, or as blooming single stem plants in 6 cm. cells for use in planters. Due to the short internodes, it can be easily controlled in early propagations by growth regulators. Minneken has excellent keeping qualities and early flowering plants can be held for later sales. There will have to be considerable research into the matter of flower initiation under natural day lengths coupled with temperatures, in comparison to controlled day length prior to initiation and at initiation. It is very apparent that Minneken is flowering earlier than most commercial cultivars under natural day length in Ohio but takes approximately the same time to develop when tested under exact controlled day lengths with other commercial cultivars. This characteristic of earlier flower initiation is of commercial significance.

(B) *Natural flowering season.*—The natural flowering season is mid to late November in Ohio. Flowering time under controlled day length at 18° C. in summer is 10 weeks, and in winter is 10 weeks. The cyathia will continue to develop and initiate until day length is greater than approximately 13 hours and temperatures are not above 27° C.

(C) *Cyathia.*—The cyathia are rounded and yellow-green in color, turning yellow near the tip, with a pinkish cast at the tip. Borne on 5 to 10 mm. yellow-green stems.

(D) *Borne.*—Involucre is flat with only slight reflexing. Cyathias stay clustered in the center of the bract and do not grow apart (split). The cyathias are tolerant of stresses such as high temperature, low light and low nutrition without dropping.

(E) *Quantity.*—Highly dependent on cultural practices and varies from 10 to more than 25. Cyathias continue to develop over a period of several months.

(F) *Bracts.*—The last true leaves tend to become pink, with the first to start turning having a green midrib. The primary bracts are 10 to 11 cm. long and 5.5 to 6.0 cm. wide at the broadest point, with petioles 2.3 to 3 cm. long, being ovate in shape. Secondary bracts are 6 to 7 cm. long and 3 to 4 cm. wide with petioles 0.5 to 1.0 cm. long as measured on an unpinched plant. The dimensions will be somewhat smaller on plants grown under similar conditions. The diameter of the bract head is 20 to 25 cm. on a non-pinched plant and 15 to 20 cm. on a pinched plant. The bract size will vary depending upon nutrition, temperatures, light, and other cultural practices. The quantity of bracts will vary, but may be 35 or more under good cultural practices. Color: Young bracts, top side, 51C; under side 52D. Mature bracts, top side, between 48C and 49A; under side 49A.

(G) *Reproductive organs.*—(1) Stamens: Numerous; anther oblong and pinkish-red in color; filament pinkish-red; pollen yellow. (2) Pistels: Very few in number. Stigma forked, color reddish-purple; styles white with pinkish cast; ovaries, 3 celled, about 4 mm. when receptive and green in color. (3) Nectar cup: 1 per cyathia, yellow in color; generally produce ample nectar when mature.

Disease resistance: There is no evidence to date of mildew or botrytis problems. White fly has an apparent low preference to Minneken as adjacent infested cultivars did not cause buildup of egg masses on Minneken.

I claim:

1. A new and distinct cultivar of poinsettia plant named Minneken, as illustrated and described, and particularly characterized by its pink colored bracts; vigorous, dwarf growth habit; early flowering; outstanding keeping quality, and by its commercially significant ability of being grown as a single stem or pinched plant.

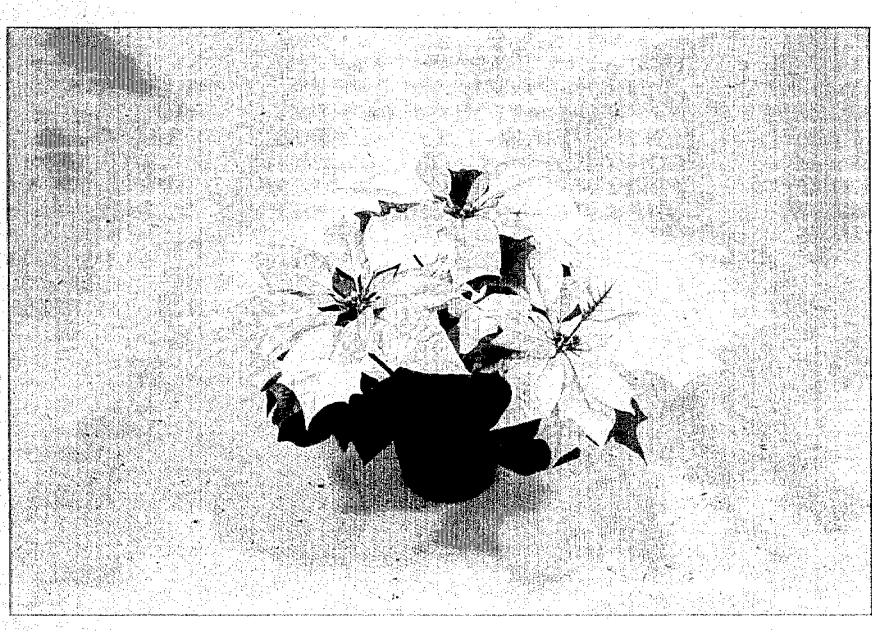

* * * * *